United States Patent [19]

Dickey

[11] Patent Number: 4,548,802
[45] Date of Patent: * Oct. 22, 1985

[54] CONTINUOUS FLOW SEPARATION WITH MOVING BOUNDARY SORPTION

[75] Inventor: Leland C. Dickey, Omaha, Nebr.

[73] Assignee: InterNorth, Inc., Omaha, Nebr.

[*] Notice: The portion of the term of this patent subsequent to Oct. 22, 2002 has been disclaimed.

[21] Appl. No.: 638,255

[22] Filed: Aug. 6, 1984

Related U.S. Application Data

[63] Continuation-in-part of Ser. No. 561,899, Dec. 15, 1983.

[51] Int. Cl.[4] .................. B01D 15/02; B01D 15/08
[52] U.S. Cl. ............................... 423/659; 55/34;
55/67; 55/77; 55/181; 55/390; 210/656;
210/670; 210/671; 210/673; 210/198.2;
423/210; 435/70; 435/174; 435/183; 435/184;
435/287; 435/803
[58] Field of Search .................. 55/34, 77–79,
55/99, 181, 390, 67, 386; 423/219, 659, 210 R,
210 S; 210/660, 670, 671, 676, 656–659, 198.2,
198.3; 435/70, 174, 183, 184, 287, 803; 422/70

[56] References Cited

U.S. PATENT DOCUMENTS

| | | | |
|---|---|---|---|
| 2,222,828 | 11/1940 | Guthrie | 55/390 |
| 2,302,807 | 11/1942 | Shoeld | 55/390 |
| 2,639,000 | 5/1953 | Edwards | 184/4.6 |
| 2,678,132 | 5/1954 | Beard | 210/670 |
| 3,335,081 | 8/1967 | El-Naggar | 210/619 |
| 3,498,026 | 3/1970 | Messinger | 55/390 |
| 3,598,726 | 8/1971 | Welch | 210/619 |
| 3,757,492 | 5/1971 | Graff | 55/181 |
| 3,907,967 | 9/1975 | Filss | 423/210 S |
| 4,083,778 | 4/1978 | McGrew | 210/671 |
| 4,242,107 | 12/1980 | Jenkins | 55/390 |
| 4,292,054 | 9/1981 | Noack | 55/181 |
| 4,302,222 | 11/1981 | Miller | 55/390 |
| 4,324,564 | 4/1982 | Oliker | 55/20 |
| 4,348,290 | 9/1982 | Schipper | 210/783 |
| 4,351,650 | 9/1982 | Shinoda | 55/181 |
| 4,353,720 | 10/1982 | Margraf | 55/262 |
| 4,391,616 | 7/1983 | Imamura | 55/390 |
| 4,415,342 | 11/1983 | Foss | 55/96 |

FOREIGN PATENT DOCUMENTS

| | | | |
|---|---|---|---|
| 3102280 | 8/1982 | Fed. Rep. of Germany | 55/77 |
| 4638241 | 12/1969 | Japan | 210/670 |
| 46-18547 | 5/1971 | Japan | 210/671 |
| 1339621 | 12/1973 | United Kingdom | 55/390 |

OTHER PUBLICATIONS

Perry's Chemical Engineers Handbook, McGraw Hill, Fourth Edition, 1969, 16–20.

*Primary Examiner*—Ernest G. Therkorn
*Attorney, Agent, or Firm*—Donald F. Haas

[57] ABSTRACT

A continuous process for separating components of a fluid mixture is disclosed which comprises forming a sorption zone and a desorption zone, said sorption and desorption zones being separated by a boundary of a sorbent material which continuously moves back and forth between the sorption and desorption zones, causing a fluid mixture to flow into the sorption zone wherein the conditions are such to promote sorption of one of the components of the mixture by the sorbent material, and creating conditions in the desorption zone such that the sorbed component will be desorbed when the sorbent material containing the sorbed component moves into the desorption zone. This sorption separation process is used in a network (including a linear series) of sorption/desorption units for separation of multiple components of fluid mixtures or for more complete separation of one component of a fluid mixture.

4 Claims, 3 Drawing Figures

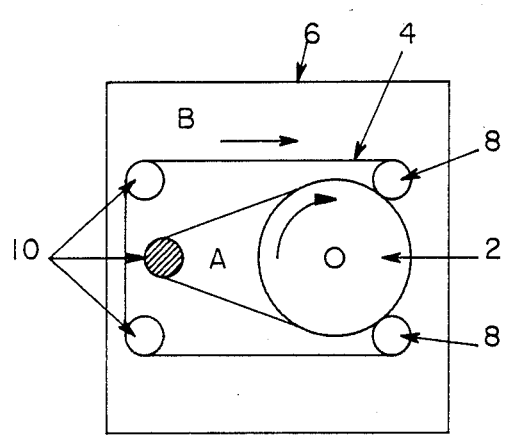
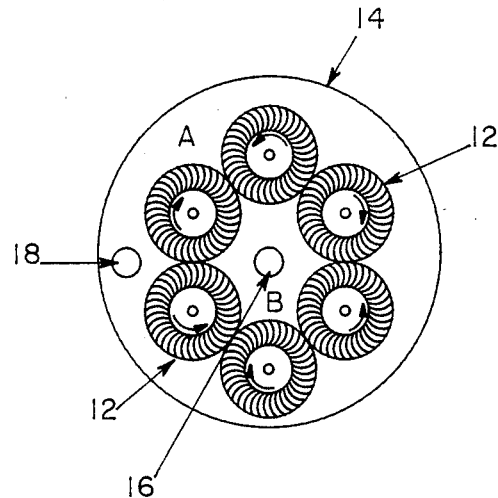
FIG. 1    FIG. 2
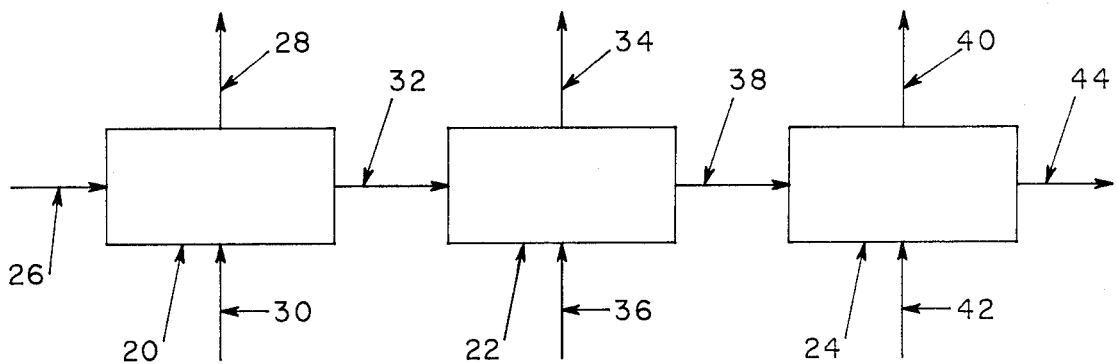
FIG. 3

CONTINUOUS FLOW SEPARATION WITH MOVING BOUNDARY SORPTION

REFERENCE TO RELATED APPLICATION

This application is a continuation-in-part of my application entitled "Continuous Flow Separation or Mixing with Moving Boundary Sorption", Ser. No. 561,899, filed Dec. 15, 1983. This application is currently pending before the Patent & Trademark Office.

BACKGROUND OF THE INVENTION

This invention relates to a continuous process for obtaining optimal separation of a fluid mixture by sorption. The method also relates to a process for preparing precise fluid mixtures where the metered component is mixed by moving boundary sorption. Specifically, the method relates to the separation of fluid mixtures wherein more than one sorption apparatus is connected in a network.

In recent years, cyclic separation processes have received considerable attention. Such processes as pressure-swing adsorption, parametric pumping, and cycling zone adsorption, separate continuous or semi-continuous fluid feed streams by cycling a thermodynamic variable which affects the mass transfer of fluid components with a sorption media. The cycle is designed to alternately sorb and desorb components so the fluid components are separated and the media returns to its initial condition after the completion of a cycle. The feed and product streams can be rendered continuous by combining sorption units in parallel but each unit necessarily experiences discontinuous flow conditions so that the sorbing media can be altered by changing thermodynamic variables such as temperatures, pH, or pressure, for example, and so that the other product stream can be created thereby. The discontinuity of flow through or past the sorbing media creates inefficiency in the separations because of the mixing of fluid elements tht have been exposed to the sorbing media under different conditions.

All practical separation techniques that occur with discontinuous flow result in product reservoir mixing. Since the feed mixture flows through the vessel during the sorption cycle of the cycling process, the sorbent will fill with the sorbed fluid component and the sorptivity will decrease. Thus, fluid entering the vessel early in the cycle is stripped of the sorbable constitutents to a greater extent than fluid entering late in the cycle. As a result, the composition of the fluid emerging from the sorbent zone is continually changing. Such a system cannot be controlled as efficiently as a single condition, continuous, time invariant process because in the cyclic operation you must compromise between optimizing for the early portion of the sorption cycle and the later portion. The ideal situation where product flow streams are not mixed would require a prohibitively large number of separate reservoirs as well as a complicated flow management system.

It is an object of the present invention to provide a method for continuous flow separation or mixing which avoids the inefficiencies inherent in reservoir mixing. It is a further object of the present invention to provide a continuous method of flow separation or mixing wherein the only seal between the sorption and desorption zones is the sorption media itself. It is a further object of the present invention to provide more than one moving boundary sorption separator so that more than one sorbent or more than one set of conditions can be used in the separation of fluid mixtures.

SUMMARY OF THE INVENTION

The present invention relates to a continuous process for separating components of a fluid mixture which comprises first forming at least one sorption zone and at least one desorption zone. The sorption and desorption zones are separated by a boundary of a sorbent material which continuously moves back and forth between the sorption and desorption zones. A fluid mixture is caused to flow into the sorption zone wherein the conditions are such to promote sorption of at least one of the components of the mixture by the sorbent material. Finally, conditions are created in the desorption zone such that the sorbed component will be desorbed when the sorbent material containing it moves into the desorption zone. The product from at least one of the zones is then conveyed to another separator wherein the preceding steps are repeated. These steps can be repeated in as many other separators as are desired.

In another embodiment of the present invention, the desorbed component forms a part of a second fluid mixture which is present in the desorption zone. In such a situation, the desorption zone can be a reaction zone wherein the rate of reaction is controlled by the amount of desorbed component which enters the desorption zone.

BRIEF DESCRIPTION OF THE DRAWINGS

FIG. 1 is a cross section of a desorption apparatus illustrating the use of a large sorbent roller in combination with a moving belt to define the sorption and desorption zones.

FIG. 2 is a cross section of an apparatus containing six soft rollers which are either constructed of a sorbent material or are coated with such a material.

FIG. 3 illustrates the arrangement of a multiplicity of moving boundary separators in use in a network.

DETAILED DESCRIPTION OF THE INVENTION

As stated above, the process of the present invention provides a continuous method for separating components of a fluid mixture. The invention requires that separate chambers be connected by a rotatable sorbent barrier which will continuously alternate the sorbent face exposed to each chamber. The rotation rate will be varied to optimize separation in conjunction with the fluid stream throughput and the sorption/desorption conditions.

As stated above, a fluid mixture is caused to flow into the sorption zone wherein the conditions are such to promote sorption of one of the components of the mixture by the sorbent material. Then conditions are created in the desorption zone to promote the desorbing of the sorbed component when the sorbent material containing it moves into the desorption zone. Thermodynamic variables such as temperature and pressure can be used to influence the sorption and desorption of the component of the original fluid mixture. Other variables such as pH, concentration of other chemical species, or voltage can also be used to influence the sorption/desorption process. Examples of fluid separations which can be performed according to the method of the present invention are aqueous acetic acid, aqueous glucose and fructose, enzyme mixtures in aqueous solution, dipeptides in aqueous solution, and any gas mixture where one component or group of components can be selectively sorbed. Hydrogen and water can be readily removed from nonpolar gases such as power plant exhaust gases.

The fact that the separator elements can be held at a steady sorption condition allows them to be deliberately adjusted and thus act as analytical instruments. Sorption type analytical separations are conventionally carried out by chromatography or sometimes with a series of filters. My invention has a potential advantage over these "linear" methods in that a branched separation scheme can be constructed with flow switches and sorption parameters in the network controlled manually or automatically using information from on-line sensors. The sorption character of the early (initially encountered) moving boundary separators would be of a general nature and the composition could be "scanned" by having a parameter, such as sorption temperature for example, automatically increase or decrease until a product (or products) is sensed in the desorption stream. Once products were sensed in this stream, a valve would direct it to another separator whose sorption parameters would be adjusted based on the information generated by the preceding sensors. The stream carrying the originally unsorbed components would be sent to a separator whose sorption parameters could likewise be controlled.

A machine based on such a scheme would be particularly useful for separation of complex mixtures containing a large number of species such as biological mixtures. Parameter and switch control could be carried out by computer. It would be desirable to have a diluent fluid that could be cleanly separated from or added to the mixture. Water would be an obvious diluent for many aqueous solutions. Since the mixture components fed are not consumed by the sorption process, if non-degradative-type sensing such as spectrophotometry is used, all product streams could be returned to the feed supply vessel to reconstitute the feed. Thus with appropriate diluent addition and/or removal as needed to fill the separators and interconnecting lines, the reconstituted sample could be reseparated with different initial sorption conditions and the original analysis confirmed or not. The retesting capability would be especially advantageous when calibrating the machine with known compounds and mixtures since the sorption dependence on conditions could be determined and logged into the computer memory in a straightforward manner.

A machine to produce purified pharmaceuticals or fine chemicals could be designed after the sorption network described above. It would have advantage of being readily adjusted to produce various chemicals so that the process streams might change weekly or daily without machine alterations other than sorption conditions in the separators and flow control changes. To produce a pure stream output the sorbent boundary rotation rate and sorption conditions would be adjusted to give the sharpest separation of the desired component in the pure product stream and the other stream would be partly recycled to the optimized separator, as necessary to increase yield of the desired product. This product stream could in turn be directed to a second separator and the stream refined further in the same manner and so on to a limit set by the amount of the desired component left to purify.

Finally, a reactive system could be organized using a similar sorption network scheme. In this case the sorption process would involve sorption/reaction on the moving boundary, for example, a surface containing immobilized enzymes, with products being desorbed and either separated in a downstream sorption separator or reacted further in following sorption reactors. The system would not be limited to the use of sorption separator elements. If appropriate, conventional process elements such as membrane separation, dialysis or precipitation units, could be included in the overall process.

Reactive processes based on use of immobilized cells or even enzyme mixes are especially dependent on rapid and efficient removal of biological and particularly cellular products because of the presence of over-product inhibitory processes which cut off further reaction and either destroy the desired product or create undesired byproducts at a certain level of product in the environment. The sorptivity of the separator element can be viewed as a simple analog to the permeability of the cell membrane. The sorption separator selectively transports compounds with an affinity to the sorbent to a new environment, disengages them and returns to the sorption zone. In a cell, this function is performed by extremely specific molecules imbedded in the cell wall.

The process of the present invention can also be used to mix fluid components together. Mixing is accomplished in exactly the same manner as separation—the difference is only in which side of the process, sorption or desorption, is considered the product stream. The mixing mode is useful in preparing precise fluid mixtures where the metered component is carried into the desorption or product chamber by the sorbent material. The product chamber might in fact be a reaction chamber where the feed of the sorbent-carried reactant is rate controlling. An example of this is partial oxidation of hydrocarbons in which oxygen is transported from an air chamber to a reaction chamber by a sorbent material. In this case, both chambers could be at high pressure because the absorbed oxygen would be desorbed by reaction rather than partial pressure reduction as in the case of other fluid separations. The pressure of the two chambers should be nearly equal to minimize gas leakage or pumping by the moving elements.

The moving boundary separators are connected in a network according to the present invention so that different components of a fluid mixture can be selectively absorbed in each of the separators. The network can be a linear series as shown in FIG. 3. This process performs a similar function as that performed in a continuous chromatograph but does not require cyclic operation to produce the continuous effect. The conditions in each of the separators, i.e. rate of rotation, temperature, pressure, flow rate, pH, sorbent, etc., can be adjusted independently for the sorption of different components of a fluid mixture or for optimal separation of progressively lower concentrations of the same sorbed material.

For the purposes of this invention sorbent materials are generally of four types:
1. Solids which can absorb gases in the bulk of the material. For example FeTi, LaNi$_5$, and the other so-called metal hydrides can absorb hydrogen. Solids which a high specific surface such as Fuller's earths, bauxite, alumina, gas adsorbent carbon, silica gel and zeolites (aluminosilicates) can be used. In some of these latter examples considerable temperature elevation is required to regenerate the adsorptivity. This might necessitate some modification of the apparatus design so that the desorption chambers can withstand the heat.

2. Porous insoluble solids containing absorbent liquids, such as carboxy-methyl cellulose (CMC)/water, or saponified starch-g-polyacrylonitrile, (HSPAN)/water, can be used. In either case the water is strongly bound to the solid but is still as absorptive as pure water. Other polar solvents or aqueous solutions could be used with these solids (CMC or HSPAN) but is likely that modification of the constituent solid would be the preferred way to optimize a particular gas absorption application. Generally, the polarity of the solid should match that of the chosen absorbent liquid to maximize liquid content in the sorbent combination. Consequently, various hydrocarbon-swellable polyolefins would provide suitable mechanical support for alkanes or other nonpolar liquids.

3. Gels formed from solvents and soluble solids such as polymers of soluble monomers can also be used. The distinction from (2) is that in this case the solid does not provide any structural form and therefore the gel can be applied as a coating to an existing solid or possibly cast into appropriate form. Examples are protein/water, poly-saccharide/water, cellulose acetate/water, ABS polymers/ketones, and polystyrene/aromatic solvents.

4. Solids formed from a combination of fluids that solidify under conditions in the sorption chamber, especially where one of the fluids is the sorbed component, can be used. This is the most complicated case from the standpoint of designing a process in which the sorption phase seals the chambers. However, it is the only one where elasticity of the sorbent will not be necessary to achieve a tight fit between the moving elements. Examples would be hydrate formation or reversible polymerization of a fluid monomer being removed from a mixture with nonpolymerizable components. It is possible that if one of the combining components is more or less permanently fixed to the moving element, e.g. water in the case of hydrate formulation, it could be supported in or with a solid material such as cases (2) and (3) above.

It is very important to the present invention that the sorbent material provides the seal which separates the sorption zone from the desorption zone. In order to accomplish this, the sorbent material may be deformable so that it can provide an acceptable seal. The separation between the sorption and desorption zones can be provided by a combination of one or more rollers and one or more moving belts and also by the combination of two or more moving belts without any rollers. In the first case, either the rollers or the belts, or both, may have the sorbent material at least on the surfaces thereof and in the latter case, one, part, or all of the belts may have the sorbent material thereon. In fact, it is possible to use more than one type of sorbent so that more than one selectivity for the sorbed component is possible with the apparatus of this invention. There may instead be disposed between the sorption and desorption zones a series of rotating rollers which have the sorbent material at least on the surfaces thereof and which are in engagement in series so that the sorbent material forms the boundary seal between the sorption and desorption zones. The number of rollers is necessarily even and four or more. The rollers need not all be alike or even symmetrical so long as they form a boundary composed of rotatable elements. The important aspect of all of the embodiments of this invention is that the rollers of belts be in engagement so that the sorbent material forms the boundary between the sorption and desorption zones.

FIG. 1 illustrates one particular embodiment of the present invention wherein a large roller 2 which contains or is coated with the sorbent material is used in combination with a moving belt 4 to define a desorption zone A. The belt 4 and the outer housing 6 define sorption zone B. Rollers 8 maintain the belt 4 in engagement with the large roller 2 and guide rollers 10 assist in positioning the belt 4 properly.

FIG. 2 illustrates another embodiment of the present invention wherein six flexible rotating rollers 12 are disposed within a housing 14. The rollers 12 are either formed of a flexible sorbent material or are coated therewith. Again, the sorbent material provides the seal between sorption zone B and desorption zone A. The feed gas enters the sorption zone inlet 16 and the desorbed components exit the apparatus through the desorption zone outlet 18.

FIG. 3 illustrates how three moving boundary separators 20, 22, and 24 are used in series for the separation of fluid mixtures. The separators may be constructed as shown in FIG. 1 or 2 or as shown in any of the embodiments disclosed in my copending application entitled "Continuous Flow Separation or Mixing with Moving Boundary Sorption", Ser. No. 561,899, filed Dec. 15, 1983 and copending allowed application "Continuous Flow Separation with Moving Boundary Sorption", Ser. No. 638,283, filed concurrently herewith.

In one use of the process of the present invention, a fluid mixture to be treated enters separator 20 through feed line 26 and the component to be separated leaves through line 28. If it is desired to use a carrier fluid in the desorption of any of the separators, then such carrier will enter through carrier feed line 30. The rest of the feed fluid mixture exits the separator 20 through line 32 and is conveyed to separator 22.

Separator 22 may utilize a different sorbent or may have different operating conditions such as those mentioned above. Its purpose may be to separate the same component that was separated in separator 20 or its purpose may be to separate a different component of the original fluid mixture. The desorption product leaves through line 34. If a carrier fluid is necessary, then it will enter through line 36. The remainder of the fluid mixture leaves separator 22 through line 38 and is conveyed to separator 24 wherein a further separation takes place and the desorption product leaves through line 40. Optional carrier fluid will enter through line 42. What is left of the fluid mixtures leaves separator 24 through line 44.

EXAMPLE I

As a continuous analog to a liquid affinity chromotographic separation, a crude extract of glycogen metabolism enzymes is fed under ambient, neutral pH conditions to a series of four sorbent separators. The sorbent is a methyl amine substituted sepharose gel. The amount of methyl amine substitution in the sorbent sepharose increased from 10 millimoles of methyl amine/liter of sepharose for the first separator to 20, 30 and 40 millimoles for the succeeding separators. The desorption side of the separator is rinsed with a 120 millimolar NaCl solution. Essentially pure side streams of the compounds phosphorylase kinase, glycogen synthetase, phosphorylase b and phosphorylase phosphatase in aqueous solution are produced from each separator in the order listed with protein kinase and any other non-sorbed enzymes remaining in the stripped stream.

EXAMPLE II

A low capacity sorbent is used to coat the moving separator surface such that the exchange surface in the first separator is completely filled during the sorption cycle by the most readily sorbed component of the feed mixture. The second separator sorbent surface is then covered (filled) by the most readily sorbed component remaining in the feed stream and so forth. The capacity of each separator must closely match the amount of component to be sorbed in the stream fed to it. On line increase of the capacity is possible, within limits, by increasing the rotation rate. For the separation of cations from an aqueous solution a resin prepared by surface sulfonation of a sytrene divinyl benzene copolymer (2% VCB) as described in *Analytical Chemistry*, 47, 1906 (1975) is used as the sorbent. The sorbed cation can be desorbed by rinsing with a dilute acid solution such as 0.1N HCl. The separation sharpness is dependent on the ion mixture fed to the separator and the feed rate and can readily be optimized by adjusting the rotation rate and recycle (if appropriate) in response to monitors on the product stream such as conductometric sensors.

EXAMPLE III

The process of Example II can also be used for aqueous anion separation using a similar low capacity ion exchange resin as sorbent. Displacement of the sorbed anions is achieved with weakly solvated salts such as sodium carbonate.

EXAMPLE IV

A continuous separation process analogous to size exclusion chromatography (formerly gel permeation chromatography) can be easily devised based on a moving boundary separator network. The essential feature of this type of separation is that the thickness of the sorbent layer is such that the time for the most permeable component of the mixture fed to diffuse through the sorbent is the same as the fluid residence time in the separator. Thus in a series of separators, the smallest, most permeable component will be almost fully sorbed, with smaller amounts of sorption by larger molecules. The desorbed stream from the first separator will contain all of the smallest sorbed component and possibly some larger compounds which can be removed by passage of this stream through a second separator with the same size exclusion chromotograpy-type sorbent, such as a polymeric coating with a narrow molecular weight and pore size distribution, with slightly different sorbent conditions or rotation rate to eliminate the impurities (larger molecules). Succeeding separators will operate in the same manner, each optimized on the most throughly sorbed component in its feed.

I claim:

1. A continuous process for separating components of a fluid mixture which comprises:
    a. Forming at least one sorption zone and at least one desorption zone in a first separator comprising at least one roller, at least one belt, or a combination of at least one roller and one belt, at least one of the belts and rollers having sorbent material thereon in engagement so that the sorbent material forms a boundary seal between the sorption and desorption zones, said sorption material continuously moving back and forth between the sorption and desorption zones,
    b. Causing a fluid mixture to flow into the sorption zone wherein the conditions are such to promote sorption of at least one of the components of the mixture by the sorbent material,
    c. Creating conditions in the desorption zone such that the sorbed component will be desorbed when the sorbent material containing the sorbed component moves into the desorption zone, and
    d. Conveying the product from at least one of said zones to at least one other separator and repeating steps a, b and c therein.

2. The process of claim 1 wherein the desorbed component forms a part of a second fluid mixture which is present in the desorption zone.

3. The process of claim 2 wherein the desorption zone is a reaction zone and the rate of reaction is controlled by the amount of desorbed component which enters the desorption zone.

4. The process of claim 1 wherein there is disposed between the sorption and desorption zones a number of rotating rollers which have the sorbent material at least on the surface thereof and which contact each other to form the sorption and desorption zones.

* * * * *